United States Patent
Tamura et al.

(10) Patent No.: US 11,453,687 B2
(45) Date of Patent: Sep. 27, 2022

(54) PRODUCTION METHOD OF BIARYLPHOSPHINE

(71) Applicant: NIPPON CHEMICAL INDUSTRIAL CO., LTD., Tokyo (JP)

(72) Inventors: Ken Tamura, Tokyo (JP); Yuki Sawatsugawa, Tokyo (JP); Natsuhiro Sano, Tokyo (JP)

(73) Assignee: NIPPON CHEMICAL INDUSTRIAL CO., LTD., Tokyo (JP)

( * ) Notice: Subject to any disclaimer, the term of this patent is extended or adjusted under 35 U.S.C. 154(b) by 0 days.

(21) Appl. No.: 17/600,251

(22) PCT Filed: Mar. 30, 2020

(86) PCT No.: PCT/JP2020/014640
§ 371 (c)(1),
(2) Date: Sep. 30, 2021

(87) PCT Pub. No.: WO2020/203988
PCT Pub. Date: Oct. 8, 2020

(65) Prior Publication Data
US 2022/0169667 A1 Jun. 2, 2022

(30) Foreign Application Priority Data

Apr. 5, 2019 (JP) .............................. JP2019-072470

(51) Int. Cl.
*C07F 9/50* (2006.01)
(52) U.S. Cl.
CPC ...................................... *C07F 9/50* (2013.01)
(58) Field of Classification Search
None
See application file for complete search history.

(56) References Cited

U.S. PATENT DOCUMENTS

2009/0221820 A1  9/2009  Buchwald et al.

FOREIGN PATENT DOCUMENTS

| JP | 2011-508726 A | 3/2011 |
| WO | 00/02887 A2 | 1/2000 |
| WO | 02/085838 A1 | 10/2002 |
| WO | 2004/052939 A2 | 6/2004 |
| WO | 2006/074315 A2 | 7/2006 |
| WO | 2009/076622 A2 | 6/2009 |

OTHER PUBLICATIONS

Arrechea et al., "Biaryl Phosphine Based Pd(II) Amido Complexes: The Effect of Ligand Structure on Reductive Elimination", Journal of the American Chemical Society, 2016, vol. 138, pp. 12486-12493, w/Supporting Information, pp. S54-S57, cited in ISR (12 pages).
Hoshiya et al., "An Improved Synthesis of BrettPhos- and RockPhos-Type Biarylphosphine Ligands", Advanced Synthesis & Catalysis, 2012, vol. 354, pp. 2031-2037, cited in Specification (7 pages).
Fors et al., "A Highly Active Catalyst for Pd-Catalyzed Amination Reactions: Cross-Coupling Reactions Using Aryl Mesylates and the Highly Selective Monoarylation of Primary Amines Using Aryl Chlorides", Journal of the American Chemical Society, 2008, vol. 130, pp. 13552-13554, cited in Specification (3 pages).
International Search Report dated Jun. 30, 2020, issued in counterpart International Application No. PCT/JP2020/014640 (2 pages).

*Primary Examiner* — Joseph R Kosack
(74) *Attorney, Agent, or Firm* — WHDA, LLP

(57) ABSTRACT

A production method by which a biarylphosphine useful as a Buchwald phosphine ligand can be obtained in high purity is provided through an industrially advantageous process. The production method of a biarylphosphine comprises a step A of reacting a lithiated product obtained through lithiation of a halogenated benzene derivative with a benzene derivative to obtain a biphenyl derivative, and a step B of the reacting the biphenyl derivative with a halogenated phosphine. In the step A, the charge molar ratio of the halogenated benzene derivative to the benzene derivative is preferably 1.0 to 5.0.

15 Claims, No Drawings

PRODUCTION METHOD OF BIARYLPHOSPHINE

TECHNICAL FIELD

The present invention relates to a production method of a biarylphosphine useful as a Buchwald phosphine ligand.

BACKGROUND ART

A group of Professor Buchwald of the Massachusetts Institute of Technology proposed a series of electron-rich and bulky phosphines (for example, Patent Literature 1 to 5). These are referred to as Buchwald phosphine ligands, of which functions to govern formation of various bonds such as C—C, C—N, and C—O bonds have been attracting attention.

As Buchwald phosphine ligands, biarylphosphines such as t-BuBretPhos, RockPhoss, and BrettPhos are known.

As a production method of these biarylphosphines, for example, in the following Patent Literature 5, Non-Patent Literature 1 and Non-Patent Literature 2, a method including a step of reacting with a Grignard reagent according to a reaction scheme 1 is proposed.

[Chemical Formula 1]

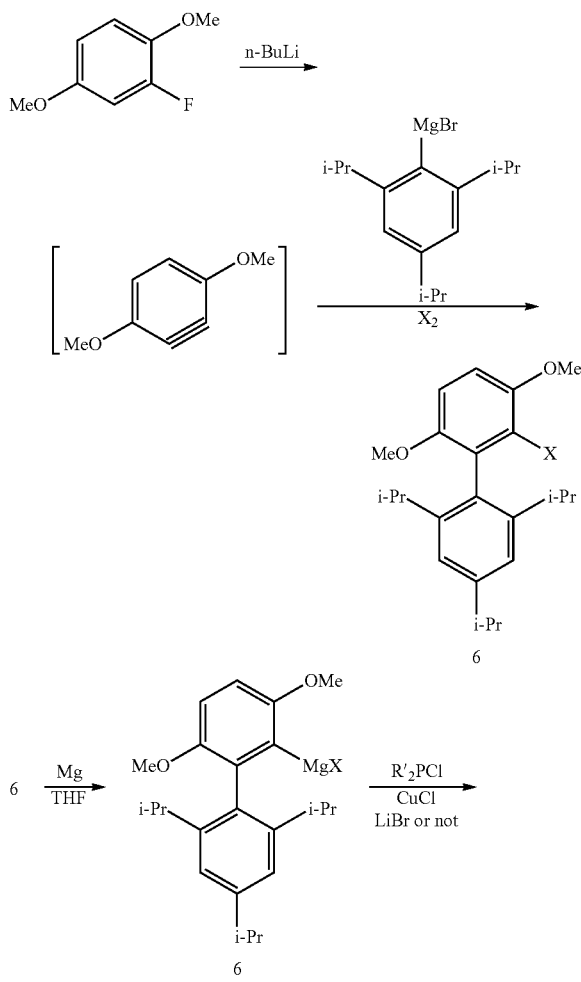

However, since a Grignard reagent is used in Patent Literature 5, Non-Patent Literature 1 and Non-Patent Literature 2, a step of separately adjusting the reagent is required, so that reactions and treatment of by-products are complicated, which is not industrially advantageous. In addition, it has been necessary to once isolate an intermediate (a compound 6 in the reaction scheme 1) in order to remove by-products for enhancing the purity.

CITATION LIST

Patent Literature

Patent Literature 1: International Publication No. WO 2000/02887
Patent Literature 2: International Publication No. WO 2002/085838
Patent Literature 3: International Publication No. WO 2004/052939
Patent Literature 4: International Publication No. WO 2006/074315
Patent Literature 5: International Publication No. WO 2009/076622

Non Patent Literature

Non Patent Literature 1: Advanced Synthesis & Catalysis, 2012, 354, 2031-2037 Non Patent Literature 2: Journal of the American Chemical Society, 2008, 130, 13552-S.I.

SUMMARY OF INVENTION

Technical Problem

An object of the present invention, therefore, is to provide a production method of a biarylphosphine useful as a Buchwald phosphine ligand by a more convenient and industrially advantageous process.

Solution to Problem

As a result of extensive research in view of the problems, the present inventors have found that a target biarylphosphine represented by the following general formula (5) can be obtained in high purity by performing a series of steps including at least a step of reacting a lithiated product obtained through lithiation of a halogenated benzene derivative represented by the following general formula (1) with a benzene derivative represented by the following general formula (2), and thus the present invention has been completed.

Accordingly, a first invention provided by the present invention relates to a production method of a biarylphosphine comprising:

a step A of reacting a lithiated product obtained through lithiation of a halogenated benzene derivative represented by the following formula (1):

[Chemical Formula 2]

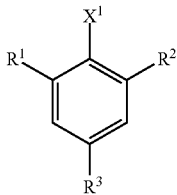

(1)

wherein $R^1$ to $R^3$ represent an alkyl group, a cycloalkyl group, an aryl group, a heteroaryl group, an aralkyl group, a heteroaralkyl group, an alkoxy group or an amino group, and the alkyl group, the cycloalkyl group, the aryl group, the heteroaryl group, the aralkyl group, the heteroaralkyl group, the alkoxy group and the amino group may be substituted with an alkyl group, a cycloalkyl group, a halogen group or an alkoxy group; $R^1$ to $R^3$ may be a same group or a different group; and $X^1$ represents a halogen atom;

with a benzene derivative represented by the following general formula (2):

[Chemical Formula 3]

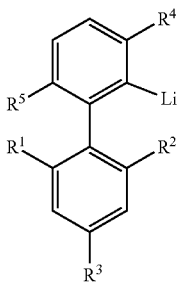

(2)

wherein $R^4$ to $R^5$ represent an alkyl group, an alkoxy group, a cycloalkyl group, an aryl group, a heteroaryl group, an aralkyl group, a heteroaralkyl group or an amino group; and the alkyl group, the cycloalkyl group, the aryl group, the heteroaryl group, the aralkyl groups, the heteroaralkyl group, the alkoxy groups and the amino group may be substituted with an alkyl group, a cycloalkyl group, a halogen groups or an alkoxy groups; $R^4$ to $R^5$ may be a same group or a different group; and $X^2$ represents a halogen atom;

to obtain a biphenyl derivative represented by a following general formula (3):

[Chemical Formula 4]

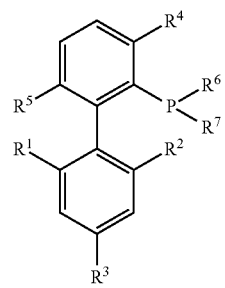

(3)

wherein $R^1$ to $R^5$ are the same as described above;

and a subsequent step B of reacting the biphenyl derivative with a halogenated phosphine represented by a following general formula (4):

$$(R^6)(R^7)PX^3 \quad (4)$$

wherein $R^6$ to $R^7$ represent an alkyl group, a cycloalkyl group, an aryl group, a heteroaryl group, an aralkyl group or a heteroaralkyl group; and $R^6$ to $R^7$ may be a same group or a different group; the alkyl group, the cycloalkyl group, the aryl group, the heteroaryl group, the aralkyl group, and the heteroaralkyl group may be substituted with an alkyl group, a cycloalkyl group, a halogen group or an alkoxy group; and $X^3$ represents a halogen atom;

the biarylphosphine being represented by a following formula (5):

[Chemical Formula 5]

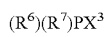

(5)

wherein $R^1$ to $R^7$ are the same as described above.

A second invention provided by the present invention relates to a production method of a biarylphosphine comprising:

a step A of reacting a lithiated product obtained through lithiation of a halogenated benzene derivative represented by the following formula (1):

[Chemical Formula 6]

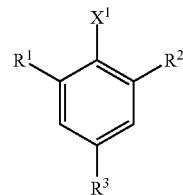

(1)

wherein $R^1$ to $R^3$ represent an alkyl group, a cycloalkyl group, an aryl group, a heteroaryl group, an aralkyl group, a heteroaralkyl group, an alkoxy group or an amino group, and the alkyl group, the cycloalkyl group, the aryl group, the heteroaryl group, the aralkyl group, the heteroaralkyl group, the alkoxy group and the amino group may be substituted with an alkyl group, a cycloalkyl group, a halogen group or an alkoxy group; $R^1$ to $R^3$ may be a same group or a different group; and $X^1$ represents a halogen atom;

with a benzene derivative represented by the following general formula (2):

[Chemical Formula 7]

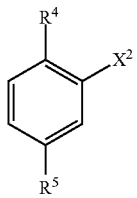

(2)

wherein $R^4$ to $R^5$ represent an alkyl group, an alkoxy group, a cycloalkyl group, an aryl group, a heteroaryl group, an aralkyl group, a heteroaralkyl group or an amino group; and the alkyl group, the cycloalkyl group, the aryl group, the heteroaryl group, the aralkyl groups, the heteroaralkyl group, the alkoxy groups and the amino group may be substituted with an alkyl group, a cycloalkyl group, a halogen groups or an alkoxy groups; $R^4$ to $R^5$ may be a same group or a different group; and $X^2$ represents a halogen atom;

to obtain a biphenyl derivative represented by a following general formula (3):

[Chemical Formula 8]

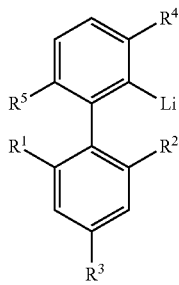

(3)

wherein $R^1$ to $R^5$ are the same as described above;

a subsequent step C of reacting the biphenyl derivative with a brominating agent or an iodinating agent to obtain a halogenated biphenyl derivative represented by the following general formula (6):

[Chemical Formula 9]

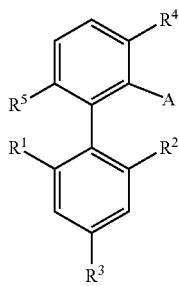

(6)

wherein $R^1$ to $R^5$ are the same as described above, and A represents a bromine atom or an iodine atom;

and a subsequent step D of reacting a lithiated product obtained through lithiation of the halogenated biphenyl derivative with a halogenated phosphine represented by a following general formula (4):

$$(R^6)(R^7)PX^3 \quad (4)$$

wherein $R^6$ to $R^7$ represent an alkyl group, a cycloalkyl group, an aryl group, a heteroaryl group, an aralkyl group or a heteroaralkyl group; and $R^6$ to $R^7$ may be a same group or a different group; the alkyl group, the cycloalkyl group, the aryl group, the heteroaryl group, the aralkyl group, and the heteroaralkyl group may be substituted with an alkyl group, a cycloalkyl group, a halogen group or an alkoxy group; and $X^3$ represents a halogen atom;

the biarylphosphine being represented by a following formula (5):

[Chemical Formula 10]

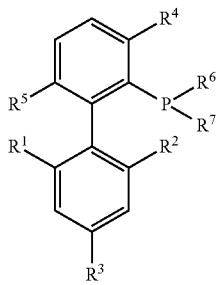

(5)

wherein $R^1$ to $R^7$ are the same as described above.

A third invention provided by the present invention relates to a production method of a halogenated biphenyl derivative comprising:

a step A of reacting a lithiated product obtained through lithiation of a halogenated benzene derivative represented by the following formula (1):

[Chemical Formula 11]

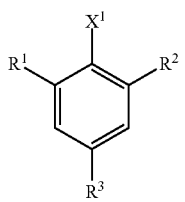

(1)

wherein $R^1$ to $R^3$ represent an alkyl group, a cycloalkyl group, an aryl group, a heteroaryl group, an aralkyl group, a heteroaralkyl group, an alkoxy group or an amino group, and the alkyl group, the cycloalkyl group, the aryl group, the heteroaryl group, the aralkyl group, the heteroaralkyl group, the alkoxy group and the amino group may be substituted with an alkyl group, a cycloalkyl group, a halogen group or an alkoxy group; $R^1$ to $R^3$ may be a same group or a different group; and $X^1$ represents a halogen atom;

with a benzene derivative represented by the following general formula (2):

[Chemical Formula 12]

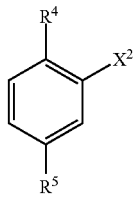

(2)

wherein $R^4$ to $R^5$ represent an alkyl group, an alkoxy group, a cycloalkyl group, an aryl group, a heteroaryl group, an aralkyl group, a heteroaralkyl group or an amino group; and the alkyl group, the cycloalkyl group, the aryl group, the heteroaryl group, the aralkyl groups, the heteroaralkyl group, the alkoxy groups and the amino group may be substituted with an alkyl group, a cycloalkyl group, a halogen groups or an alkoxy groups; $R^4$ to $R^5$ may be a same group or a different group; and $X^2$ represents a halogen atom;

to obtain a biphenyl derivative represented by a following general formula (3):

[Chemical Formula 13]

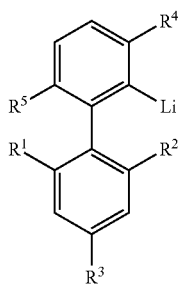

(3)

wherein $R^1$ to $R^5$ are the same as described above;

and a subsequent step D of reacting the biphenyl derivative with a brominating agent or an iodinating agent;

the halogenated biphenyl derivative being represented by a following formula (6):

[Chemical Formula 14]

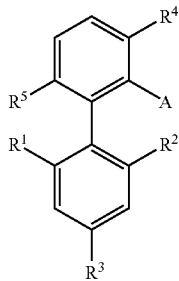

(6)

wherein $R^1$ to $R^5$ are the same as described above, and A represents a bromine atom or an iodine atom.

Advantageous Effect of Invention

According to the present invention, biarylphosphines useful as a Buchwald phosphine ligand can be obtained in good purity by an industrially advantageous process.

DESCRIPTION OF EMBODIMENT

The present invention is described based on the preferred embodiment thereof as follows.

The step A in the present invention is a step of reacting a lithiated product obtained through lithiation of a halogenated benzene derivative represented by the general formula (1) with a benzene derivative represented by the general formula (2) to obtain a biphenyl derivative represented by the general formula (3).

Examples of $R^1$ to $R^3$ in the general formula (1) include an alkyl group, a cycloalkyl group, an aryl group, a heteroaryl group, an aralkyl group, a heteroaralkyl group, an alkoxy group and an amino group.

Examples of the alkyl group include a straight-chain or branched alkyl group, having preferably 1 to 12 carbon atoms, more preferably 1 to 8 carbon atoms. Specific examples include a methyl group, an ethyl group, an n-propyl group, an iso-propyl group, an n-butyl group, a 2-butyl group, an iso-butyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, and a 5-methylpentyl group.

Examples of the cycloalkyl group include a cycloalkyl group having 3 to 16 carbon atoms. Specific examples include a cyclopropyl group, a cyclobutyl group, a cyclopentyl group, a cyclohexyl group, a 2-methylcyclopentyl group, a 3-methylcyclopentyl group, a cycloheptyl group, a 2-methylcyclohexyl group, a 3-methylcyclohexyl group, and a 4-methylcyclohexyl group. The cycloalkyl groups also include a polycyclic alkyl group. Examples thereof include a menthyl group, a bornyl group, a norbornyl group, and an adamantyl group.

Examples of the aryl group include a phenyl group having 6 to 16 carbon atoms. Specific examples thereof include a phenyl group, a 4-methylphenyl group, a 3-methylphenyl group, a 2-methylphenyl group, and a naphthyl group.

Preferred examples of the heteroaryl group include a 5-membered or 6-membered monocyclic aromatic heterocyclic group and a polycyclic aromatic heterocyclic group. Examples of the heteroaryl group include an aromatic heterocyclic group containing 1 to 3 heteroatoms such as nitrogen atoms, oxygen atoms and/or sulfur atoms. Specific examples thereof include a pyridyl group, an imidazolyl group, a thiazolyl group, a furfuryl group, a pyranyl group, a furyl group, a benzofuryl group and a thienyl group.

Examples of the aralkyl group include an aralkyl group having 7 to 12 carbon atoms. Specific examples include a benzyl group, a 2-phenylethyl group, a 1-phenylpropyl group, a 2-phenylpropyl group, a 3-phenylpropyl group, a 1-phenylbutyl group, a 2-phenylbutyl group, a 3-phenylbutyl group, a 4-phenylbutyl group, a 1-phenylpentyl group, a 2-phenylpentyl group, a 3-phenylpentyl group, a 4-phenylpentyl group, a 5-phenylpentyl group, a 1-phenylhexyl group, a 2-phenylhexyl group, a 3-phenylhexyl group, a 4-phenylhexyl group, a 5-phenylhexyl group, and a 6-phenylhexyl group.

The heteroaralkyl group has a structure in which an alkyl group is bonded to a heteroaryl group. Examples of the heteroaralkyl group include a heteroaralkyl group having 6 to 16 carbon atoms. Specific examples thereof include a 2-pyridylmethyl group, a 4-pyridylmethyl group, an imidazolylmethyl group, and a thiazolylethyl group.

The alkoxy group is a group in which the above-described alkyl group, the cycloalkyl group, the aryl group, the heteroaryl group, the aralkyl group or the heteroaralkyl group is bonded through oxygen. Examples thereof include a methoxy group, an ethoxy group, a phenyloxy group, a benzyloxy group, and a p-methoxybenzyloxy group.

The alkyl group, the cycloalkyl group, the aryl group, the heteroaryl group, the aralkyl group, the heteroaralkyl group, the alkoxy group and the amino group may further have a substituent. Examples of the substituent include an alkyl group, a cycloalkyl group, a halogen group, and an alkoxy group. Examples of the alkyl group, the cycloalkyl group, the halogen group, and the alkoxy group as the substituent include those similar to the types of $R^1$ to $R^3$ described above. Among those, a straight-chain or branched alkyl group having 1 to 10 carbon atoms is preferred as the substituent.

$R^1$ to $R^3$ in the general formula (1) each may be a same group or may be a different group. It is preferable that $R^1$ to $R^3$ be the same group. In particular, in the present production method, it is preferable that $R^1$ to $R^3$ be an iso-propyl group from the viewpoint of producing a biarylphosphine useful as a Buchwald phosphine ligand. Examples of the type of $X^1$ in the general formula (1) include a halogen atom such as fluorine, chlorine, and bromine.

Examples of $R^4$ to $R^5$ in the general formula (2) include an alkyl group, an alkoxy group, a cycloalkyl group, an aryl group, a heteroaryl group, an aralkyl group, a heteroaralkyl group, and an amino group.

Examples of the alkyl group include a straight-chain or branched alkyl group having preferably 1 to 12 carbon atoms, more preferably 1 to 8 carbon atoms. Specific examples thereof include a methyl group, an ethyl group, an n-propyl group, an iso-propyl group, an n-butyl group, a 2-butyl group, an iso-butyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a tert-hexyl group, a 2-methylpentyl group, a 3-methylpentyl group, a 4-methylpentyl group, and a 5-methylpentyl group.

Examples of the cycloalkyl group include a cycloalkyl group having 3 to 16 carbon atoms. Specific examples thereof include a cyclopropyl group, a cyclobutyl group, a cyclopentyl group, a cyclohexyl group, a 2-methylcyclopentyl group, a 3-methylcyclopentyl group, a cycloheptyl group, a 2-methylcyclohexyl group, a 3-methylcyclohexyl group, and a 4-methylcyclohexyl group. The cycloalkyl group also include a polycyclic alkyl group. Examples thereof include a menthyl group, a bornyl group, a norbornyl group, and an adamantyl group.

Examples of the aryl group include a phenyl group having 6 to 16 carbon atoms. Specific examples thereof include a phenyl group, a 4-methylphenyl group, a 3-methylphenyl group, a 2-methylphenyl group, and a naphthyl group.

Preferred examples of the heteroaryl group include a 5-membered or 6-membered monocyclic aromatic heterocyclic group or a polycyclic aromatic heterocyclic group.

Examples of the heteroaryl group include an aromatic heterocyclic group containing 1 to 3 heteroatoms such as a nitrogen atom, an oxygen atom and/or a sulfur atom. Specific examples thereof include a pyridyl group, an imidazolyl group, a thiazolyl group, a furfuryl group, a pyranyl group, a furyl group, a benzofuryl group and a thienyl group.

Examples of the aralkyl group include an aralkyl group having 7 to 12 carbon atoms. Specific examples thereof include a benzyl group, a 2-phenylethyl group, a 1-phenylpropyl group, a 2-phenylpropyl group, a 3-phenylpropyl group, a 1-phenylbutyl group, a 2-phenylbutyl group, a 3-phenylbutyl group, a 4-phenylbutyl group, a 1-phenylpentyl group, a 2-phenylpentyl group, a 3-phenylpentyl group, a 4-phenylpentyl group, a 5-phenylpentyl group, a 1-phenylhexyl group, a 2-phenylhexyl group, a 3-phenylhexyl group, a 4-phenylhexyl group, a 5-phenylhexyl group, and a 6-phenylhexyl group.

Examples of the heteroaralkyl group include a heteroaralkyl group having 6 to 16 carbon atoms, and specific examples thereof include a 2-pyridylmethyl group, a 4-pyridylmethyl group, an imidazolylmethyl group, and a thiazolylethyl group.

The alkoxy group is a group in which the above-described alkyl group, the cycloalkyl group, the aryl group, the heteroaryl group, the aralkyl group, or the heteroaralkyl group is bonded through oxygen, and examples thereof include a methoxy group, an ethoxy group, and a phenyloxy group. Examples thereof include a benzyloxy group and a p-methoxybenzyloxy group.

The alkyl group, the cycloalkyl group, the aryl group, the heteroaryl group, the aralkyl group, the heteroaralkyl group, the alkoxy group and the amino group may further have a substituent. Examples of the substituent include an alkyl group, a cycloalkyl group, a halogen group, and an alkoxy group. Incidentally, examples of the alkyl group, the cycloalkyl group, the halogen group, and the alkoxy group as the substituent include those similar to the types of $R^4$ to $R^5$ described above. Among those, a straight-chain or branched alkyl group having 1 to 10 carbon atoms is preferred as the substituent.

$R^4$ to $R^5$ in the general formula (2) may be a same group or a different group. In particular, in the present production method, it is preferable that $R^4$ to $R^5$ be a methyl group or a methoxy group from the viewpoint of producing a biarylphosphine useful as a Buchwald phosphine ligand. From the similar viewpoint, it is preferable that $R^4$ to $R^5$ be the same group. Examples of the type of $X^2$ in the general formula (2) include a halogen atom such as fluorine, chlorine, and bromine.

In the reaction operation of the step A, a halogenated benzene derivative represented by the general formula (1) is lithiated to prepare a solution containing the resulting lithiated product (hereinafter, also referred to as "liquid a" in some cases). Further, separately from the liquid a, a solution containing a benzene derivative represented by the general formula (2) (hereinafter, also referred to as "liquid b" in some cases) is prepared. It is preferable that a reaction be subsequently performed by adding the liquid b to the liquid a, or by adding the liquid a to the liquid b.

The liquid a is a solution containing a lithiated product of a halogenated benzene derivative, obtained by adding a lithiating agent to a liquid containing a halogenated benzene derivative represented by the general formula (1). It is preferable that the concentration of the halogenated benzene derivative represented by the general formula (1) in the liquid a be 1 mass % to 30 mass %, particularly 5 mass % to 20 mass %, from the viewpoint of enhancing the reactivity, and the viewpoint of controlling by-products.

As the lithiating agent for the liquid a, for example, an organic lithium compound is used. Examples of the organic lithium compound include methyllithium, ethyllithium, n-propyllithium, sec-propyllithium, n-butyllithium, sec-butyllithium, and tert-butyllithium. Among those, n-butyllithium is preferred from the viewpoints of appropriate basicity and sufficient reactivity.

It is preferable that the amount of the lithiating agent added be 2.0 to 7.0, particularly 2.1 to 6.5, in terms of the molar ratio of the lithiating agent to the halogenated benzene derivative represented by the general formula (1), from the viewpoints of economy and reactivity.

The solvent that may be used in the liquid a is not particularly limited as long as it is a solvent that can dissolve a halogenated benzene derivative represented by the general formula (1) and a lithiated product to be produced, and is inert to the reaction. Examples of the solvent include tetrahydrofuran, cyclopentyl methyl ether, tert-butyl methyl ether, 1,2-dimethoxyethane, N,N-dimethylformamide, diethyl ether, dibutyl ether, dioxane, hexane, and toluene. These solvents may be used alone or as a mixed solvent. In particular, tetrahydrofuran is preferred from the viewpoint of solubility of the lithiated product.

The addition temperature of the lithiating agent is preferably set at −80 to 20° C., more preferably −80 to −10° C. from the viewpoint of controlling by-products. By adding a lithiating agent to a liquid containing a halogenated benzene derivative represented by the general formula (1), the halogenated benzene derivative represented by the general formula (1) is rapidly lithiated. On an as needed basis, an aging reaction may be continuously performed after completion of addition of the lithiating agent in order to complete the lithiation reaction.

The liquid b is a solution dissolving a benzene derivative represented by the general formula (2) in a solvent. It is preferable that the concentration of the benzene derivative represented by the general formula (2) in the liquid b be set at 5 mass % to 90 mass %, particularly 10 mass % to 50 mass %, from the viewpoints of reactivity and controlling by-products.

The solvent usable for the liquid b is not particularly limited as long as it is a solvent that can dissolve a benzene derivative represented by the general formula (2), and is inert to the reaction. Examples of the solvent include tetrahydrofuran, cyclopentyl methyl ether, tert-butyl methyl ether, 1,2-dimethoxyethane, N,N-dimethylformamide, diethyl ether, dibutyl ether, dioxane, hexane, and toluene. These solvents may be used alone or as a mixed solvent. In particular, tetrahydrofuran is preferred from the viewpoint of polarity and solubility.

It is preferable that mixing of the liquid a and the liquid b be performed such that the charge molar ratio of a halogenated benzene derivative represented by the general formula (1) in the liquid a to a benzene derivative represented by the general formula (2) in the liquid b is set at 1.0 to 5.0, from the viewpoint of improving the yield while controlling the by-products.

In particular, in the case where the present production method is performed according to "production method (1)" described below, it is preferable that liquid a and the liquid b be added such that the charge molar ratio of a halogenated benzene derivative represented by the general formula (1) in the liquid a to a benzene derivative represented by the general formula (2) in the liquid b is controlled to 1.0 to 5.0, particularly 1.0 to 3.0, especially 1.2 to 2.5, from the viewpoint of improving the yield and economy.

Also, in the case where the present production method is performed according to "production method (2)" described below, it is preferable that addition be performed in the same manner, such that the charge molar ratio of a halogenated benzene derivative represented by the general formula (1) in the liquid a to a benzene derivative represented by the general formula (2) in the liquid b is controlled to 1.0 to 5.0, particularly 1.0 to 3.0, especially 1.2 to 2.5, from the viewpoint of improving the yield and economy.

The rate of addition of the liquid a and/or the liquid b is not particularly limited. From the viewpoint of obtaining a target product with stable quality, it is preferable that addition is performed at a constant rate. The addition of the liquid a and/or the liquid b may be continuous or intermittent. It is preferable that the internal temperature of the mixed liquid during mixing of the liquid a and the liquid b be maintained within a preferable range of addition temperature of the liquid a or the liquid b described below.

It is preferable that the addition temperature of the liquid a and the liquid b be each independently controlled to −80 to 20° C., particularly −80 to −10° C., from the viewpoint of obtaining a target product of high purity in high yield.

After mixing the liquid a and the liquid b, on an as needed basis, an aging reaction may be continuously performed to complete the reaction. It is preferable that the temperature of the aging reaction be set at −80 to 20° C., particularly −80 to −10° C., from the viewpoint of accelerating the reaction and controlling by-products. The completion of the aging reaction may be confirmed by the presence or absence of a benzene derivative represented by (2) through gas chromatography analysis. The reaction time for obtaining a satisfactory target product is usually 1 hour or more, preferably 3 to 12 hours, though depending on reaction conditions, etc.

In the present production method, after the step A, the following (1) including a step B (hereinafter, referred to as "production method (1)" in some cases) or the following (2) including the steps C to D (hereinafter, referred to as "production method (2)" in some cases) is performed to produce a biarylphosphine represented by the general formula (5), which is the target product of the present production method.

<Production Method (1)>

The step B is a step of producing a target biarylphosphine represented by the general formula (5) by reacting the biphenyl derivative obtained in the step A with the halogenated phosphine represented by the general formula (4) according to the following reaction scheme 2:

[Chemical Formula 15]

Reaction Scheme (2)

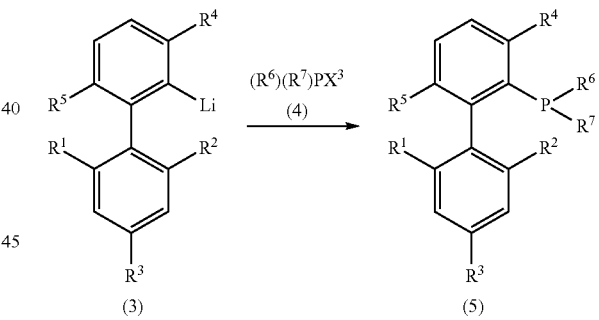

wherein $R^1$ to $R^7$ and $X^3$ are the same as described above.

In the present production method, the step B may be a reaction in succession with the step A, or after completion of the step A, a biphenyl derivative represented by the general formula (3) recovered from the reaction liquid may be purified on an as needed basis, and then subjected to the step B.

$R^6$ and $R^7$ in the formula of a halogenated phosphine represented by the general formula (4) represent an alkyl group, a cycloalkyl group, an aryl group, a heteroaryl group, an aralkyl group or a heteroaralkyl group.

Examples of the alkyl group include a straight-chain or branched alkyl group having preferably 1 to 12 carbon atoms, more preferably 1 to 8 carbon atoms. Specific examples thereof include a methyl group, an ethyl group, an n-propyl group, an iso-propyl group, an n-butyl group, a 2-butyl group, an iso-butyl group, a tert-butyl group, an n-pentyl group, a 2-pentyl group, a tert-pentyl group, a 2-methylbutyl group, a 3-methylbutyl group, a 2,2-dimethylpropyl group, an n-hexyl group, a 2-hexyl group, a 3-hexyl group, a tert-hexyl group, a 2-methylpentyl group, 3-methylpentyl group, a 4-methylpentyl group, and a 5-methylpentyl group.

Examples of the cycloalkyl group include a cycloalkyl group having 3 to 16 carbon atoms. Specific examples thereof include a cyclopropyl group, a cyclobutyl group, a cyclopentyl group, a cyclohexyl group, a 2-methylcyclopentyl group, a 3-methylcyclopentyl group, a cycloheptyl group, a 2-methylcyclohexyl group, a 3-methylcyclohexyl group, and a 4-methylcyclohexyl groups. The cycloalkyl group also includes a polycyclic alkyl group. Examples thereof include a menthyl group, a bornyl group, a norbornyl group, and an adamantyl group.

Examples of the aryl group include a phenyl group having 6 to 16 carbon atoms. Specific examples thereof include a phenyl group, a 4-methylphenyl group, a 3-methylphenyl group, a 2-methylphenyl group, and a naphthyl group.

Preferred examples of the heteroaryl group include a 5-membered or 6-membered monocyclic aromatic heterocyclic group or a polycyclic aromatic heterocyclic group. Examples of the heteroaryl group include an aromatic heterocyclic group containing 1 to 3 heteroatoms such as a nitrogen atom, an oxygen atom and/or a sulfur atom. Specific examples thereof include a pyridyl group, an imidazolyl group, a thiazolyl group, a furfuryl group, a pyranyl group, a furyl group, a benzofuryl group and a thienyl group.

Examples of the aralkyl group include an aralkyl group having 7 to 12 carbon atoms. Specific examples thereof include a benzyl group, a 2-phenylethyl group, a 1-phenylpropyl group, a 2-phenylpropyl group, a 3-phenylpropyl group, a 1-phenylbutyl group, a 2-phenylbutyl group, a 3-phenylbutyl group, a 4-phenylbutyl group, a 1-phenylpentyl group, a 2-phenylpentyl group, a 3-phenylpentyl group, a 4-phenylpentyl group, a 5-phenylpentyl group, a 1-phenylhexyl group, a 2-phenylhexyl group, a 3-phenylhexyl group, a 4-phenylhexyl group, a 5-phenylhexyl group, and a 6-phenylhexyl group.

Examples of the heteroaralkyl group include a heteroaralkyl group having 6 to 16 carbon atoms, and specific examples thereof include a 2-pyridylmethyl group, a 4-pyridylmethyl group, an imidazolylmethyl group, and a thiazolylethyl group.

The alkyl group, the cycloalkyl group, the aryl group, the heteroaryl group, the aralkyl group and the heteroaralkyl group may further have a substituent. Examples of the substituent include an alkyl group, a cycloalkyl group, a halogen group, and an alkoxy group. Examples of the alkyl group, the cycloalkyl group, the halogen group, and the alkoxy group as the substituent include those similar to the types of $R^6$ and $R^4$ described above. In particular, it is preferable that the substituent be a straight-chain or branched alkyl group having 1 to 10 carbon atoms. Examples of the alkyl group, the cycloalkyl group, the halogen group, and the alkoxy group as the substituent include those similar to the types of $R^6$ and $R^7$ described above. In particular, it is preferable that the substituent be a straight-chain or branched alkyl group having 1 to 10 carbon atoms.

$R^6$ to $R^7$ in the general formula (4) may be the same group or different group. It is preferable that $R^6$ to $R^7$ be the same group. In particular, in the present production method, it is preferable that $R^6$ to $R^7$ be an adamantyl group, a tert-butyl group or a cyclohexyl group from the viewpoint of producing a biarylphosphine useful as a Buchwald phosphine ligand. Examples of the type of $X^3$ in the general formula (1) include a halogen atom such as fluorine, chlorine, and bromine.

In the step B, it is preferable that the biphenyl derivative obtained in the step A be reacted with a halogenated phosphine represented by the general formula (4) in a solvent. The solvent that may be used in the step B is not particularly limited as long as it is a solvent that can dissolve a biphenyl derivative represented by the general formula (3), and is inert to a halogenated phosphine of the general formula (4) and a biarylphosphine represented by the general formula (5). Examples of the solvent include tetrahydrofuran, cyclopentyl methyl ether, tert-butyl methyl ether, 1,2-dimethoxyethane, N,N-dimethylformamide, diethyl ether, dibutyl ether, dioxane, hexane, and toluene. These solvents may be used alone or as a mixed solvent. In particular, tetrahydrofuran is preferred from the viewpoint of polarity and solubility.

The amount of the halogenated phosphine of the general formula (4) added is set at 1.0 to 3.0, preferably 1.0 to 1.5, in terms of the molar ratio of the halogenated phosphine of the general formula (4) to the biphenyl derivative represented by the general formula (3), from the viewpoint of economy and reactivity.

The reaction temperature in the step B is set at preferably −50 to 80° C., particularly −30 to 50° C., from the viewpoints of accelerating the reaction and controlling by-products.

The completion of the reaction in the step B may be confirmed by the presence or absence of a biphenyl derivative represented by (3) through gas chromatography analysis. The reaction time for obtaining a satisfactory target product is usually 1 hour or more, preferably 1 to 10 hours, though depending on reaction conditions, etc.

After completion of the reaction in the step B, the resulting biarylphosphine represented by the general formula (5) may be subjected to purification such as recrystallization, column chromatography, and extraction, on an as needed basis.

<Production Method (2)>

The step C is a step of obtaining a halogenated biphenyl derivative represented by the general formula (6) by reacting the biphenyl derivative obtained in the step A with a brominating agent or an iodinating agent according to the following reaction scheme 3:

[Chemical Formula 16]

Reaction Scheme (3)

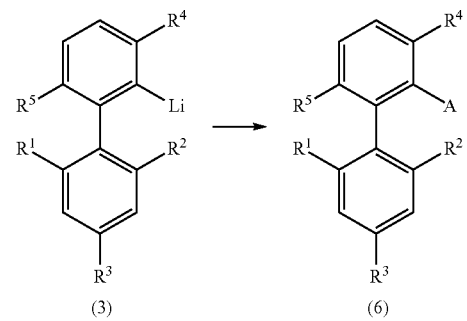

wherein $R^1$ to $R^5$ are the same as described above, and A represents a bromine atom or an iodine atom.

In the present production method, it is preferable that the step C be a reaction performed in succession with the step A.

Examples of the iodinating agent according to the step C include iodine, N-iodosuccinimide, sodium iodide, and potassium iodide, and among them, iodine is preferably used from the viewpoint of general-purpose raw material at low cost. Examples of the brominating agent include bromine, N-bromosuccinimide, phosphorus tribromide, and potassium bromide, and among them, bromine is preferably used from the viewpoint of general-purpose raw material at low cost.

It is preferable that the amount of the brominating agent or the iodinating agent added be set at 1.0 to 5.0, particularly 1.0 to 2.0, in terms of molar ratio of the brominating agent or the iodinating agent to the biphenyl derivative represented by the general formula (3), from the viewpoint of economy and reactivity.

In the step C, it is preferable that the biphenyl derivative obtained in the step A be reacted with a brominating agent or an iodinating agent in a solvent. The solvent usable in the step C is not particularly limited, as long as the solvent can dissolve a biphenyl derivative represented by the general formula (3), and is inert to a biphenyl derivative represented by the general formula (3) and a biphenyl derivative represented by the general formula (6). Examples of the solvent include tetrahydrofuran, cyclopentyl methyl ether, tert-butyl methyl ether, 1,2-dimethoxyethane, N,N-dimethylformamide, diethyl ether, dibutyl ether, dioxane, hexane, and toluene. These solvents may be used alone or as a mixed solvent. Among these, tetrahydrofuran is particularly preferred from the viewpoint of reactivity.

The reaction temperature in the step C is preferably −80 to 50° C., more preferably −20 to 20° C., from the viewpoint of controlling reactivity and side reactions.

Completion of the reaction in the step C may be confirmed by the presence or absence of the biphenyl derivative represented by (3) through gas chromatography analysis. The reaction time for obtaining a satisfactory target product is usually 1 hour or more, preferably 1 to 10 hours, though depending on reaction conditions, etc.

The step D is a step of producing a target biarylphosphine represented by the general formula (5) according to the following reaction scheme 4, by lithiating the biphenyl bromide derivative or the biphenyl iodide derivative obtained in the step C with a lithiating agent, and then reacting the lithiated product with a halogenated phosphine represented by the general formula (4):

[Chemical Formula 17]

Reaction Scheme (4)

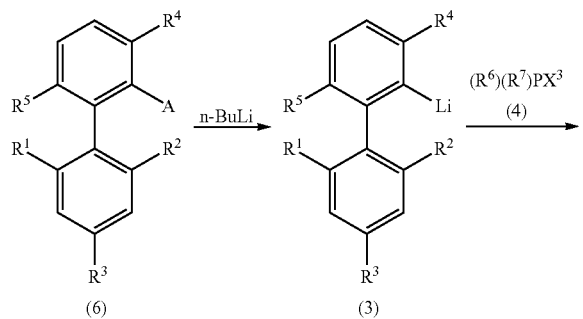

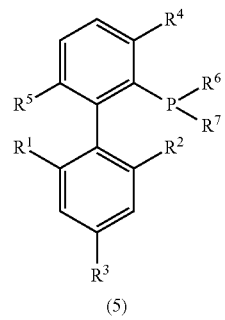

wherein the $R^1$ to $R^7$, $X^3$ and A are the same as described above.

In the present production method, the step D may be a reaction in succession with the step C, or after completion of the step C, a halogenated biphenyl derivative represented by the general formula (6) recovered from the reaction liquid may be purified on an as needed basis, and then subjected to the step D.

As $R^6$ and $R^7$ in the formula of a halogenated phosphine represented by the general formula (4), the same ones as in the step B described above may be used.

As the lithiating agent for a biphenyl derivative represented by the general formula (6), for example, an organic lithium compound is used. Examples of the organic lithium compound include methyllithium, ethyllithium, n-propyllithium, sec-propyllithium, n-butyllithium, sec-butyllithium, and tert-butyllithium. Among these, n-butyllithium is preferred from the viewpoints of appropriate basicity and sufficient reactivity.

It is preferable that the amount of the lithiating agent added be set at 1.0 to 2.0, particularly 1.1 to 1.5, in terms of molar ratio of the lithiating agent to the biphenyl derivative represented by the general formula (6), from the viewpoints of economy and reactivity.

It is preferable that the reaction between the lithiated product of a biphenyl derivative represented by the general formula (6) and a halogenated phosphine represented by the general formula (4) be performed in a solvent. The usable solvent is not particularly limited as long as it can dissolve a halogenated biphenyl derivative represented by the general formula (6) and a lithiated product thereof, and is inert to a halogenated phosphine represented by the general formula (4) and a biarylphosphine represented by the general formula (5). Examples of the solvent include tetrahydrofuran, cyclopentyl methyl ether, tert-butyl methyl ether, 1,2-dimethoxyethane, N,N-dimethylformamide, diethyl ether, dibutyl ether, dioxane, hexane, and toluene. These solvents may be used alone or as a mixed solvent. Among these, tetrahydrofuran is particularly preferred from the viewpoints of polarity and solubility.

It is preferable that the amount of a halogenated phosphine represented by the general formula (4) added be set at 1.0 to 3.0, particularly 1.0 to 1.5, in terms of molar ratio of the halogenated phosphine represented by the general formula (4) to the halogenated biphenyl derivative represented by the general formula (6), from the viewpoints of economy and reactivity.

It is preferable that the reaction temperature in the step D be set at −50 to 80° C., particularly −30 to 50° C., from the viewpoints of accelerating the reaction and controlling by-products.

Completion of the reaction in the step D may be confirmed by the presence or absence of the biphenyl derivative represented by (3) through gas chromatography analysis. The reaction time for obtaining a satisfactory target product is usually 1 hour or more, preferably 1 to 10 hours, though depending on reaction conditions, etc.

After completion of the reaction in the step D, the resulting biarylphosphine represented by the general formula (5) may be subjected to purification such as recrystallization, column chromatography, and extraction, on an as needed basis.

The biarylphosphine represented by the general formula (5) obtained in the present production method is particularly useful as a Buchwald phosphine ligand. Further, the intermediate halogenated biphenyl derivative represented by the general formula (6) obtained in the present production method is useful as an intermediate raw material for biarylphosphines.

EXAMPLES

The present invention is described with reference to Examples as follows, though the present invention is not limited thereto.

[Chemical Formula 18]

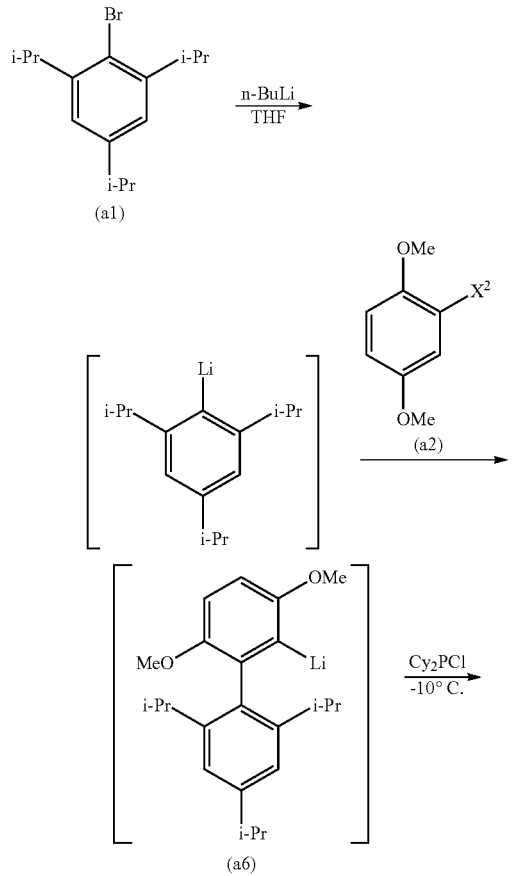

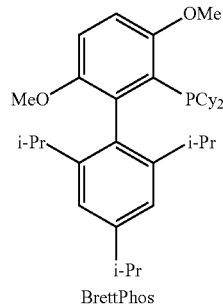

$X^2 = Cl$

<Step A>

A fully dried 1-L four-necked flask purged with nitrogen was charged with 2,4,6-triisopropylbromobenzene (a1) (56.1 g, 198 mmol) and tetrahydrofuran (450 ml). After cooling to −78° C. under nitrogen atmosphere, a hexane solution of 15 mass % of n-butyllithium (140.9 g, 330 mmol) was added dropwise thereto over 1 hour. The mixture was then aged at −78° C. for 1 hour, so that a liquid a was prepared.

In another fully dried 300-mL four-necked flask purged with nitrogen, 1-chloro-2,5-dimethoxybenzene (a2) (22.7 g, 132 mmol) was dissolved in tetrahydrofuran (120 ml), so that a liquid b was prepared. The liquid b was continuously added to the liquid a over 1 hour, such that the internal temperature was maintained at about −80° C. (reaction temperature A). The mixture was gradually heated to a temperature of −10° C. and aged for 8 hours, so that a yellow transparent liquid was obtained.

<Step B>

Chlorodicyclohexylphosphine (Cy$_2$PCl, 30.7 g, 132 mmol) was continuously added to the liquid obtained in the step A over 30 minutes, such that that the internal temperature was maintained at about −10° C. Subsequently, the mixture was aged at −10° C. for 5 hours.

When 50 g of water was added to stop the reaction, the liquid turned orange and transparent. The solvent was evaporated using a vacuum pump until the liquid volume reached 500 ml, and the reaction liquid was washed with 400 ml of 0.9 mass % of baking soda and 450 ml of water in a sequential manner, and the aqueous layer was discarded. Subsequently, when the solvent was evaporated using the vacuum pump, an orange solid was precipitated. To dissolve the precipitate, 100 ml of ethyl acetate was added, and the temperature was raised to 60° C. Further, 300 ml of methanol was continuously added while maintaining the internal temperature at about 55° C. When the liquid was gradually cooled, precipitation of crystals started at about 50° C. The liquid was further cooled to 5° C. Subsequently, the precipitate was filtered through a glass filter, rinsed with cold methanol, and then dried under reduced pressure to obtain 2-dicyclohexylphosphino-3,6-dimethoxy-2',4',6'-triisopropyl-1,1'-biphenyl (BrettPhos) (30.7 g, yield: 42.4%). The purity was 99% or more in the measurement by $^{31}$P NMR, and 99% or more also in the measurement by gas chromatography.

(Identification data of BrettPhos)

Melting point: 193 to 194° C.

1H NMR (500.15 MHz, CDCl$_3$): δ 0.95 (d, J=6.8 Hz, 6H), 1.22 (d, J=6.8 Hz, 6H), 1.33 (d, J=7.0 Hz, 6H), 1.43-0.94 (m, 10H), 1.73-1.63 (m, 6H), 1.85-1.81 (m, 2H), 2.25-2.17 (m,

2H), 2.44 (septet, J=6.8 Hz, 2H), 2.95 (septet, J=7.0 Hz, 1H), 3.56 (s, 3H), 3.83 (s, 3H), 6.80 (d, J=8.8 Hz, 1H), 6.86 (d, J=8.8 Hz, 1H), 6.89 (s, 2H);

$^{13}$C NMR (125.76 MHz, CDCl$_3$): δ 23.5, 23.9, 25.0, 26.50, 26.51, 27.4, 27.6, 27.8, 27.9, 30.4, 30.8, 30.9, 32.7, 32.9, 33.7, 36.5, 36.6, 54.5, 55.0, 108.5, 110.6, 120.0, 126.5, 126.8, 132.5, 132.6, 138.8, 139.1, 145.8, 145.9, 146.8, 152.1, 152.3, 156.2, 156.3;

$^{31}$P NMR (202.46 MHz, CDCl$_3$): δ 1.6

Example 21

BrettPhos was synthesized in the same manner as in Example 1 except that in the liquid a, the amount of 2,4,6-triisopropylbromobenzene (a1) was changed to 93.5 g (330 mmol), and in the liquid a, the amount of the hexane solution of 15 mass % of n-butyllithium was changed to 197.3 g (462 mmol). (38.7 g, yield: 54.7%).

Example 3

BrettPhos was synthesized in the same manner as in Example 1, except that in the step A, the reaction temperature A between the lithiated product of 2,4,6-triisopropyl-bromobenzene (a1) and 1-chloro-2,5-dimethoxybenzene (a2) was set at −30° C. (26.6 g, yield: 37.6%).

Example 4

[Chemical Formula 19]

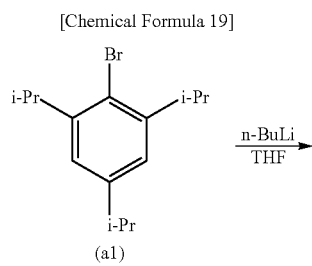
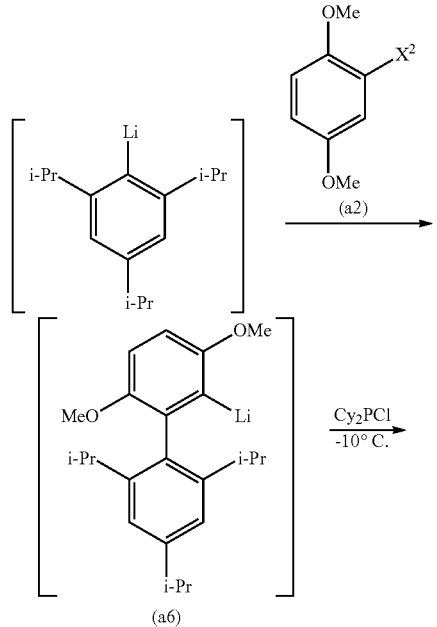

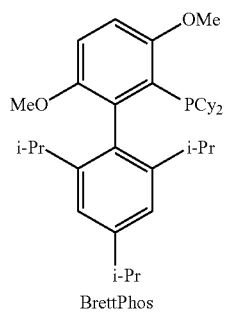

$X^2 = F$

BrettPhos was synthesized in the same manner as in Example 1, except that 1-chloro-2,5-dimethoxybenzene (a2) in the liquid b used in Example 1 was changed to 1-fluoro-2,5-dimethoxybenzene (a2) (20.6 g, 0.132 mmol). (35.1 g, yield: 49.6%).

TABLE 1

| | Charge molar ratio (a1)/(a2) | Reaction temperature A (° C.) | Type of X$^2$ in formula of (a2) | BrettPhos | |
|---|---|---|---|---|---|
| | | | | Yield (%) | Purity (%) |
| Example 1 | 1.5 | −80 | Cl | 42.4 | 99 or more |
| Example 2 | 2.5 | −80 | Cl | 54.7 | 99 or more |
| Example 3 | 1.5 | −30 | Cl | 37.6 | 99 or more |
| Example 4 | 1.5 | −80 | F | 49.6 | 99 or more |

Example 5

[Chemical Formula 20]

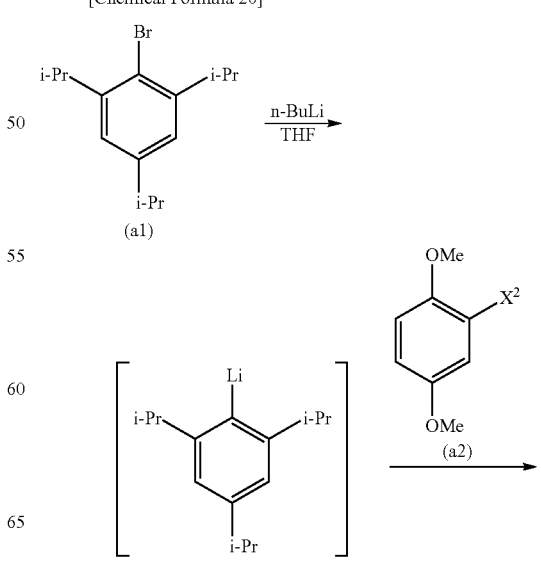

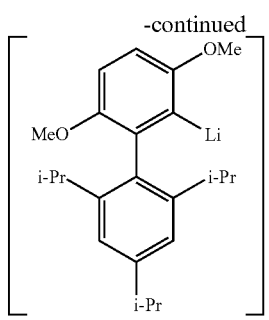

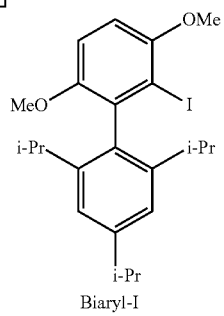

Biaryl-I $X^2 = Cl$

<Step A>

A fully dried 1-L four-necked flask purged with nitrogen was charged with 2,4,6-triisopropylbromobenzene (a1) (93.5 g, 330 mmol) and tetrahydrofuran (450 ml). After cooling to −78° C. under a nitrogen atmosphere, a hexane solution of 15 mass % of n-butyllithium (197.3 g, 462 mmol) was added dropwise thereto over 1 hour. The mixture was then aged at −78° C. for 1 hour, so that a liquid a was prepared.

In another fully dried 300-mL four-necked flask purged with nitrogen, 1-chloro-2,5-dimethoxybenzene (a2) (22.7 g, 132 mmol) was dissolved in tetrahydrofuran (120 ml), so that a liquid b was prepared. The liquid b was continuously added to the liquid a over 1 hour, such that the internal temperature was maintained at about −80° C. (reaction temperature A). The mixture was gradually heated to a temperature of −10° C. and aged for 8 hours, so that a yellow transparent liquid was obtained.

<Step C>

Iodine (67.0 g, 264 mmol) was dissolved in tert-butyl methyl ether (200 ml) in advance, and the tert-butyl methyl ether solution of iodine was slowly added dropwise to the liquid obtained in the step A at −10° C. Then, the mixture was stirred as it was for 6 hours. The organic layer was washed twice with 250 ml of an aqueous solution of 10 mass % of sodium hydrogen sulfite, then washed with 250 ml of pure water, and dried over anhydrous magnesium sulfate. After evaporating the solvent under reduced pressure, recrystallization was performed from a mixed solvent of acetic acid and methanol (1:1). The resulting crystals were rinsed with cold methanol and dried under reduced pressure to obtain 2-iodo-3,6-dimethoxy-2',4',6'-triisopropyl-1,1'-biphenyl (iodine intermediate) (42.3 g, 90.5 mmol, 68.6%). In the measurement by gas chromatography, the purity was 99% or more.

(Identification data of Biaryl-I)

Melting point: 199 to 200° C.

$^1$H NMR (500.15 MHz, CDCl$_3$): δ 0.99 (d, J=6.9 Hz, 6H), 1.17 (d, J=6.9 Hz, 6H), 1.31 (d, J=6.9 Hz, 6H), 2.36 (septet, J=6.9 Hz, 2H), 2.95 (septet, J=6.9 Hz, 1H), 3.65 (s, 3H), 3.89 (s, 3H), 6.80 (d, J=8.9 Hz, 1H), 6.89 (d, J=8.9 Hz, 1H), 7.04 (s, 2H);

$^{13}$C NMR (125.76 MHz, CDCl$_3$): δ 23.6, 24.0, 24.5, 30.8, 34.1, 55.5, 56.8, 96.4, 109.2, 110.0, 120.7, 135.9, 136.2, 145.7, 148.2, 152.3, 152.5.

Example 6

[Chemical Formula 21]

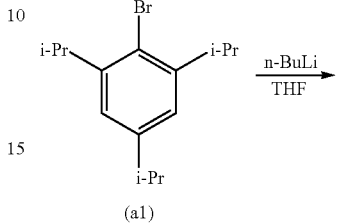

<Step D>

A fully dried 1-L four-necked flask purged with nitrogen was charged with 2-iodo-3,6-dimethoxy-2',4',6'-triisopropyl-1,1'-biphenyl (iodine intermediate) (19.3 g, 41.3 mmol) obtained in the step C of Example 5 and cyclopentyl methyl ether (200 mL), and the mixture was cooled to −30° C. under nitrogen atmosphere. Subsequently, a hexane solution of 15 mass % of n-butyllithium (18.0 g, 42.1 mmol) was added dropwise thereto over 1 hour. The mixture was then aged at −30° C. for 1 hour, and then chlorodicyclohexylphosphine ($Cy_2PCl$, 9.6 g, 41.3 mmol) was continuously added thereto over 30 minutes, such that the internal temperature was maintained at about −10° C. Then, the mixture was aged at −10° C. for 10 hours.

After 20 g of water was added to stop the reaction, the reaction liquid was washed with 100 ml of 5 mass % of baking soda and 150 ml of water in a sequential manner, and the aqueous layer was discarded. Subsequently, when the solvent was evaporated using a vacuum pump, an orange solid was precipitated. To dissolve the precipitate, 55 ml of ethyl acetate was added, and the temperature was raised to 60° C. Further, 165 ml of methanol was continuously added while maintaining the internal temperature at about 55° C. When the liquid was gradually cooled, precipitation of crystals started at about 50° C. The liquid was further cooled to 5° C. Subsequently, the precipitate was filtered through a glass filter, rinsed with cold methanol, and then dried under reduced pressure to obtain 2-dicyclohexylphosphino-3,6-dimethoxy-2',4',6'-triisopropyl-1,1'-biphenyl (BrettPhos) (16.9 g, yield: 76.3%). The purity was 99% or more in the measurement by $^{31}P$ NMR, and 99% or more also in the measurement by gas chromatography.

The invention claimed is:

1. A production method of a biarylphosphine comprising:
   a step A of preparing
   a liquid a comprising a lithiated product obtained by adding a lithiating agent to a liquid containing a halogenated benzene derivative represented by the following general formula (1):

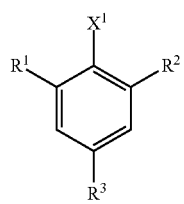

(1)

wherein $R^1$ to $R^3$ represent an alkyl group, a cycloalkyl group, an aryl group, a heteroaryl group, an aralkyl group, a heteroaralkyl group, an alkoxy group or an amino group, and the alkyl group, the cycloalkyl group, the aryl group, the heteroaryl group, the aralkyl group, the heteroaralkyl group, the alkoxy group and the amino group may be substituted with an alkyl group, a cycloalkyl group, a halogen group or an alkoxy group; $R^1$ to $R^3$ may be a same group or a different group; and $X^1$ represents a halogen atom;
   for lithiation so that a molar ratio of the lithiating agent to the halogenated benzene derivative represented by the general formula (1) is 2.0 to 7.0, and a liquid b comprising a benzene derivative represented by the following general formula (2):

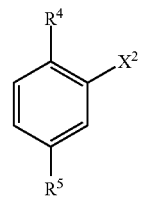

(2)

wherein $R^4$ to $R^5$ represent an alkyl group, an alkoxy group, a cycloalkyl group, an aryl group, a heteroaryl group, an aralkyl group, a heteroaralkyl group or an amino group; and the alkyl group, the cycloalkyl group, the aryl group, the heteroaryl group, the aralkyl groups, the heteroaralkyl group, the alkoxy groups and the amino group may be substituted with an alkyl group, a cycloalkyl group, a halogen groups or an alkoxy groups; $R^4$ to $R^5$ may be a same group or a different group; and $X^2$ represents a halogen atom; and mixing the liquid a and the liquid b for reaction so that a charge molar ratio of the halogenated benzene derivative represented by the general formula (1) to the benzene derivative represented by the general formula (2) is 1.2 to 3.0
   to obtain a biphenyl derivative represented by the following general formula (3):

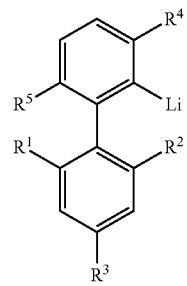

(3)

wherein $R^1$ to $R^5$ are the same as described above;
   and a subsequent step B of reacting the biphenyl derivative with a halogenated phosphine represented by the following general formula (4):

$(R^6)(R^7)PX^3$ (4)

wherein $R^6$ to $R^7$ represent an alkyl group, a cycloalkyl group, an aryl group, a heteroaryl group, an aralkyl group or a heteroaralkyl group; and $R^6$ to $R^7$ may be a same group or a different group; the alkyl group, the cycloalkyl group, the aryl group, the heteroaryl group, the aralkyl group, and the heteroaralkyl group may be substituted with an alkyl group, a cycloalkyl group, a halogen group or an alkoxy group; and $X^3$ represents a halogen atom;
   the biarylphosphine being represented by the following general formula (5):

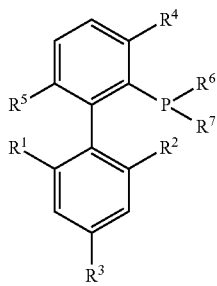

(5)

wherein $R^1$ to $R^7$ are the same as described above.

2. A production method of a biarylphosphine comprising:

a step A of preparing a liquid a comprising a lithiated product obtained by adding a lithiating agent to a liquid containing a halogenated benzene derivative represented by the following general formula (1):

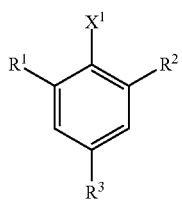

(1)

wherein $R^1$ to $R^3$ represent an alkyl group, a cycloalkyl group, an aryl group, a heteroaryl group, an aralkyl group, a heteroaralkyl group, an alkoxy group or an amino group, and the alkyl group, the cycloalkyl group, the aryl group, the heteroaryl group, the aralkyl group, the heteroaralkyl group, the alkoxy group and the amino group may be substituted with an alkyl group, a cycloalkyl group, a halogen group or an alkoxy group; $R^1$ to $R^3$ may be a same group or a different group; and $X^1$ represents a halogen atom;

for lithiation so that a molar ratio of the lithiating agent to the halogenated benzene derivative represented by the general formula (1) is 2.0 to 7.0, and a liquid b comprising a benzene derivative represented by the following general formula (2):

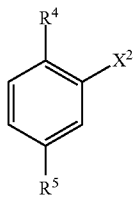

(2)

wherein $R^4$ to $R^5$ represent an alkyl group, an alkoxy group, a cycloalkyl group, an aryl group, a heteroaryl group, an aralkyl group, a heteroaralkyl group or an amino group; and the alkyl group, the cycloalkyl group, the aryl group, the heteroaryl group, the aralkyl groups, the heteroaralkyl group, the alkoxy group and the amino group may be substituted with an alkyl group, a cycloalkyl group, a halogen groups or an alkoxy groups; $R^4$ to $R^5$ may be a same group or a different group; and $X^2$ represents a halogen atom; and mixing the liquid a and the liquid b for reaction so that a charge molar ratio of the halogenated benzene derivative represented by the general formula (1) to the benzene derivative represented by the general formula (2) is 1.2 to 3.0 to obtain a biphenyl derivative represented by the following general formula (3):

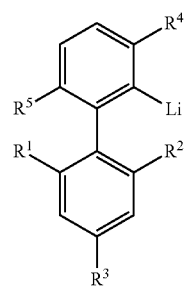

(3)

wherein $R^1$ to $R^5$ are the same as described above;

a subsequent step C of reacting the biphenyl derivative with a brominating agent or an iodinating agent to obtain a halogenated biphenyl derivative represented by the following general formula (6):

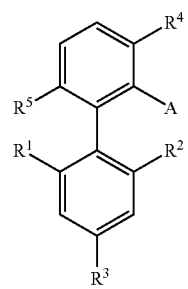

(6)

wherein $R^1$ to $R^5$ are the same as described above, and A represents a bromine atom or an iodine atom;

and a subsequent step D of reacting a lithiated product obtained through lithiation of the halogenated biphenyl derivative with a halogenated phosphine represented by the following general formula (4):

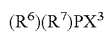

$(R^6)(R^7)PX^3$ (4)

wherein $R^6$ to $R^7$ represent an alkyl group, a cycloalkyl group, an aryl group, a heteroaryl group, an aralkyl group or a heteroaralkyl group; and $R^6$ to $R^7$ may be a same group or a different group; the alkyl group, the cycloalkyl group, the aryl group, the heteroaryl group, the aralkyl group, and the heteroaralkyl group may be substituted with an alkyl group, a cycloalkyl group, a halogen group or an alkoxy group; and $X^3$ represents a halogen atom;

the biarylphosphine being represented by the following general formula (5):

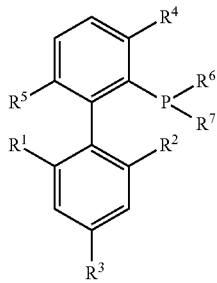

(5)

wherein $R^1$ to $R^7$ are the same as described above.

3. The production method of a biarylphosphine according to claim 1, wherein the step B is performed by a reaction in succession with the step A.

4. The production method of a biarylphosphine according to claim 1, wherein $R^1$ to $R^3$ in the formulas are the same group, and $R^4$ to $R^5$ are the same group.

5. The production method of a biarylphosphine according to claim 4, wherein $R^1$ to $R^3$ in the formulas are an iso-propyl group.

6. The production method of a biarylphosphine according to claim 4, wherein $R^4$ to $R^5$ in the formulas are a methoxy group or a methyl group.

7. The production method of a biarylphosphine according to claim 4, wherein $R^6$ to $R^7$ in the formulas are the same group.

8. The production method of a biarylphosphine according to claim 7, wherein $R^6$ to $R^7$ in the formula are an adamantyl group, a tert-butyl group or a cyclohexyl group.

9. A production method of a halogenated biphenyl derivative comprising:
a step A of preparing
a liquid a comprising a lithiated product obtained by adding a lithiating agent to a liquid containing a halogenated benzene derivative represented by the following general formula (1):

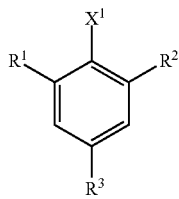

(1)

wherein $R^1$ to $R^3$ represent an alkyl group, a cycloalkyl group, an aryl group, a heteroaryl group, an aralkyl group, a heteroaralkyl group, an alkoxy group or an amino group, and the alkyl group, the cycloalkyl group, the aryl group, the heteroaryl group, the aralkyl group, the heteroaralkyl group, the alkoxy group and the amino group may be substituted with an alkyl group, a cycloalkyl group, a halogen group or an alkoxy group; $R^1$ to $R^3$ may be a same group or a different group; and
$X^1$ represents a halogen atom;
for lithiation so that a molar ratio of the lithiating agent to the halogenated benzene derivative represented by the general formula (1) is 2.0 to 7.0, and
a liquid b comprising a benzene derivative represented by the following general formula (2):

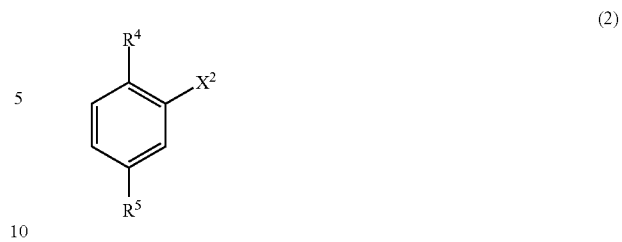

(2)

wherein $R^4$ to $R^5$ represent an alkyl group, an alkoxy group, a cycloalkyl group, an aryl group, a heteroaryl group, an aralkyl group, a heteroaralkyl group or an amino group; and the alkyl group, the cycloalkyl group, the aryl group, the heteroaryl group, the aralkyl groups, the heteroaralkyl group, the alkoxy group and the amino group may be substituted with an alkyl group, a cycloalkyl group, a halogen group or an alkoxy groups; $R^4$ to $R^5$ may be a same group or a different group; and $X^2$ represents a halogen atom; and
mixing the liquid a and the liquid b for reaction so that a charge molar ratio of the halogenated benzene derivative represented by the general formula (1) to the benzene derivative represented by the general formula (2) is 1.2 to 3.0
to obtain a biphenyl derivative represented by the following general formula (3):

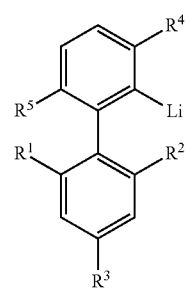

(3)

wherein $R^1$ to $R^5$ are the same as described above;
and a subsequent step C of reacting the biphenyl derivative with a brominating agent or an iodinating agent;
the halogenated biphenyl derivative being represented by the following formula (6):

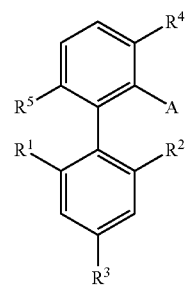

(6)

wherein $R^1$ to $R^5$ are the same as described above, and A represents a bromine atom or an iodine atom.

10. The production method of a biarylphosphine according to claim 2, wherein the step B is performed by a reaction in succession with the step A.

11. The production method of a biarylphosphine according to claim 2, wherein $R^1$ to $R^3$ in the formulas are the same group, and $R^4$ to $R^5$ are the same group.

12. The production method of a biarylphosphine according to claim 11, wherein $R^1$ to $R^3$ in the formulas are an iso-propyl group.

13. The production method of a biarylphosphine according to claim 11, wherein $R^4$ to $R^5$ in the formulas are a methoxy group or a methyl group.

14. The production method of a biarylphosphine according to claim 11, wherein $R^6$ to $R^7$ in the formulas are the same group.

15. The production method of a biarylphosphine according to claim 14, wherein $R^6$ to $R^7$ in the formula are an adamantyl group, a tert-butyl group or a cyclohexyl group.

* * * * *